United States Patent [19]

Minokani et al.

[11] Patent Number: 4,689,436

[45] Date of Patent: Aug. 25, 1987

[54] PROCESS FOR PRODUCING ALKENYL-AROMATIC HYDROCARBON DERIVATIVES

[75] Inventors: Tomiyasu Minokami; Yoshinori Saito; Toshiyuki Tsubouchi, all of Kimitsu, Japan

[73] Assignee: Idemitsu Kosan Company Limited, Tokyo, Japan

[21] Appl. No.: 861,180

[22] Filed: May 9, 1986

[30] Foreign Application Priority Data

May 13, 1986 [JP] Japan ................................. 60-101057

[51] Int. Cl.$^4$ ................................................ C07C 2/02
[52] U.S. Cl. ...................... 585/422; 585/426; 585/466
[58] Field of Search ...................... 585/422, 426, 466

[56] References Cited

U.S. PATENT DOCUMENTS

| | | | |
|---|---|---|---|
| 2,301,966 | 11/1942 | Michel et al. | 585/466 |
| 3,346,657 | 10/1967 | Henke et al. | 585/466 |
| 4,144,279 | 3/1979 | Sato et al. | 585/422 |
| 4,289,918 | 9/1981 | Sato et al. | 585/422 |

*Primary Examiner*—Curtis R. Davis
*Attorney, Agent, or Firm*—Armstrong, Nikaido, Marmelstein & Kubovcik

[57] ABSTRACT

Alkenyl-aromatic hydrocarbon derivatives are prepared by reaction of an aromatic hydrocarbon with an alkenyl-aromatic hydrocarbon in the presence of a heteropoly acid and/or a salt thereof.

16 Claims, No Drawings

PROCESS FOR PRODUCING ALKENYL-AROMATIC HYDROCARBON DERIVATIVES

BACKGROUND OF THE INVENTION

This invention relates to a novel process for producing alkenyl-aromatic hydrocarbon derivatives.

Because of their excellent solubility, aromatic compounds such as benzene, toluene, xylene and the like have heretofore been used widely as solvents for rubbers, synthetic resins, paints, agricultural chemicals such as pesticides, resin treatment of fibers, cleaning of metal parts, releasants for paints, printing ink, etc.

According to their utility, they must have a high boiling point in view of evaporation loss, safety, toxicity, evaporation rate, etc.

In order to increase the boiling point of aromatic compounds, it is known to introduce an alkyl group in an aromatic compound to form an alkyl-aromatic compound.

the introduction of an alkyl group leads to a decrease in solubility although it results in an increase in the boiling point of the resulting compound. It is often the case that the product isn't used insufficiently as a solvent depending on the purposes for which it is employed. Polychlorinated biphenyl, a typical example of a high boiling point aromatic compound, that was widely used as a heat transfer oil, an electric insulating oil, a solvent for pressure-sensitive paper, a plasticizer for rubbers and various synthetic resins, etc., have recently not been used because it has a high toxicity to humans and pollutes environment seriously. Therefore, high boiling aromatic compounds which are free of problem of environmental pollution are desired.

The alkenyl-aromatic hydrocarbon derivatives produced according to the process of this invention meet the above demand. Further, hydrogenated derivatives thereof are useful as traction drive oil.

Conventionally, alkenyl-aromatic hydrocarbon derivatives have been produced from an aromatic hydrocarbon and an alkenyl-aromatic hydrocarbon by (1) a process using a sulfuric acid having a concentration of 80 to 99% as a catalyst as described in Japanese Patent Publication No. 55-50929, or (2) a process using silica-alumina, acidic clay, zeolite exchanged for proton or a metal cation, or a strongly acidic cation exchange resin as described in Japanese Patent Publication No. 55-33692 as a catalyst.

However, those processes using sulfuric acid as a catalyst as process (1) above are disadvantageous in corrosion of apparatus due to sulfuric acid, additional steps for removal of sulfuric acid from the reaction mixture, neutralization with an alkali and washing with water long time for drying and disposing waste sulfuric acid.

Further, those processes using a solid catalyst such as a strongly acidic cation exchange resin as process (2) above, cause problems that the reaction mixture is acidic. And it is necessary to provide a step of neutralizing the mixture and the catalyst used cannot be regenerated for reuse since the catalyst is deactivated considerably during the reaction.

Moreover, solid catalysts are disadvantages in lower activity, they need a long reaction time, and yield and selectivity of a desired alkenyl-aromatic hydrocarbon are low.

As stated above, the conventional processes are not satisfactory as a process for producing alkenyl-aromatic hydrocarbon derivatives on an industrial scale.

SUMMARY OF THE INVENTION

Therefore, an object of this invention is to provide a process for producing an alkenyl-aromatic hydrocarbon derivative from an aromatic hydrocarbon and an alkenyl-aromatic hydrocarbon in the presence of a novel catalyst which is effective in a small amount, has a long duration of life, is easy to separate from a reaction product and can be recovered efficiently.

Another object of this invention is to provide a novel process for producing an alkenyl-aromatic hydrocargon derivative from an aromatic hydrocarbon and an alkenyl-aromatic hydrocarbon which process is used industrially on a large scale and enables one to recover a high quality reaction product (i.e., a mixture containing an alkenyl-aromatic hydrocarbon derivative obtained after completion of the reaction) which is neutral and contains substantially no catalyst by a simple treatment without carrying out a neutralizing treatment and washing with water.

As a result of extensive research with view to obviating the disadvantages of the conventional processes, it has now been found that heteropolyacids and its salts thereof which are known as a catalyst for dehydration reaction of alcohols, hydration reaction of olefins, alkylation reaction of aromatic hydrocarbons with aliphatic olefins (U.S. Pat. Nos. 3,346,657 and 2,301,966), hydrogenative condensation reaction of bezene (Japanese Patent Application Laid Open No. 59-5130), dehydrogenation reaction, oxidative dehydrogenation reaction, oxidation reaction, polycondensation reaction, etc., are effective as a catalyst for a process for producing an alkenyl-aromatic hydrocarbon derivative by reacting an aromatic hydrocarbon with an alkenyl-aromatic hydrocarbon.

This invention is based on the above discovery and provides a process for producing an alkenyl-aromatic hydrocarbon derivative by reacting an aromatic hydrocarbon with an alkenyl-aromatic hydrocarbon in the presence of a heteropolyacid and/or its salt as a catalyst.

DETAILED DESCRIPTION OF THE INVENTION

The term "heteropolyacid compound" as used herein refers to a heteropolyacid and/or its salt.

The process of this invention comprises reaction of an aromatic hydrocarbon with an alkenyl aromatic hydrocarbon, starting materials, in the presence of a heteropolyacid compound as a catalyst.

Suitable examples of the aromatic hydrocarbon which can be used in this invention include non-condensed aromatic hydrocarbons containing one or more benzene rings such as benzene, toluene, xylene, tetralin, alkyltetralin, etc., condensed aromatic hydrocarbons such as naphthalene, anthracene, phenanthrene, etc., mixture thereof or a fraction containing one or more of them.

There is no limitation to the manner in which the aromatic hydrocarbons are produced, and, for example, naphthalene and alkylnaphthalenes which are obtained industrially, hydrogenated products thereof, alkylation products of hydrogenated naphthalene, naphthalene fraction obtained from cracked petroleum oil and coal tar oil and hydrogenated product of such naphthalene fraction can be used.

Of the above-described aromatic hydrocarbons, preferred are those which contain Tetralin in an amount of 10 mol % or more and more preferably, 50 mol % or more.

As the alkenyl-aromatic hydrocarbons there can be used aromatic hydrocarbons in which a double bond is directly attached to the aromatic nucleus, mixtures thereof and fraction containing such.

Usually, compounds represented by general formula.

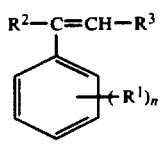

$$R^2-C=CH-R^3 \quad (I)$$

(with $(R^1)_n$ on the aromatic ring)

wherein $R^1$ represents a hydrogen atom or a lower alkyl group preferably having 1 to 4 carbon atoms, $R^2$ and $R^3$, which may be the same or different, each represents a hydrogen atom, a methyl group or an ethyl group, and n is an integer of 1 or 2, mixture thereof and fractions containing one or more of the compounds can be used as the alkenyl-aromatic hydrocarbons. When those compounds represented by general formula (I) in which $R^1$ represents a lower alkyl group having 5 or more carbon atoms or in which n is 3 or more are used, the reaction with aromatic hydrocarbons could sometimes hardly proceed.

Suitable examples of the heteropolyacid which can be used in this invention include tungsten-, molybdenum-, and vanadium-based heteropolyacids, and mixed heteropolyacids containing two or more of tungsten, molybdenum and vanadium. Salts of these heteropolyacids can also be used in the process of this invention. Preferred examples of the heteropolyacid include 12-phosphotungstic acid, 12-silicotungstic acid, 12-phosphomolybdic acid, 12-silicomolybdic acid and salts thereof which are manufactured in industrial scale and commercially available.

As for salts, acidic salts are preferred. Suitable example of the acid salt include metal cation such as sodium, potassium, lithium, cesium and the like salts.

In the process of this invention, one compound or a mixture of two or more compounds selected from all of the heteropolyacid compounds can be employed.

The heteropolyacid compounds may be one which is commercially available or products of any manufacturing methods.

Generally, the heteropolyacid compounds could contain impurities. However, they can be used as it is as far as the impurities do not affect its catalytic activity adversely. Example of such admissible impurities include phosphoric acid, oxides of phosphorus, molybdic acid, oxides of molybdenum, tungstic acid and oxides of tungsten.

In the process of this invention, it is preferred to use the heteropolyacid compound in the form of powder (smaller particle size than 60 mesh).

It is advantageous to use a heteropolyacid compound together with a solid having a smaller particle size than 16 mesh; in this case filtration of the catalyst is easier than in the case where the heteropolyacid compound is used alone. Various substances can be used as such small particle size partiles. For example, inorganic oxides such as silica, alumina, silica-alumina, slica-titania, zeolite, molecular sieves, diatomaceous earth, clay, activated carbon, carbon black, etc. can be used.

The hereropolyacid compounds can be used on a carrier.

Suitable examples of the carrier which can be used in the present invention include oxides of metals or semimetals belonging to Groups III, IV, V, VI, VII and VIII, preferably Groups III and IV, of the periodic table, complex oxides such as silica alumina, silica titania, zeolite, molecular sieves, diatomaceous earth, clay, etc., activated carbon, carbon black and the like. Example of the oxides of the elements belonging to Groups III and IV of the periodic table include silica, titania, zirconia, alumina, boria, etc. Of these carriers, silica, alumina, activated carbon, and carbon black are preferred with silica being more preferred. The carriers preferably have a pore diameter of 70 to 400 A, more preferably 100 to 200 A. However, the carrier which can be used in the process of this invention is not limited thereto and any known carriers for catalysts, regardless of whether they are organic or inorganic, can be used as a carrier for the heteropolyacid compound unless the structure of the heteropolyacid compound in a loaded state is completely destroyed.

The catalyst comprising a heteropolyacid compound supported on a carrier can be prepared by any conventional methods such as an impregnation method, a dry mixing method, a wet kneading method, etc.

The supported amount of the heteropolyacid compound varies within a wide range depending on the nature of the carrier and heteropolyacid compound used. Usually, it is 2% by weight or more, preferably 5% by weight or more, based on the weight of the carrier.

It is preferred to use the heteropolyacid compound in a supported amount of 15% by weight or more when the carrier used is alumina, activated carbon etc., or the carrier contains an inorganic component such as alumina, sodium oxide, magnesium oxide, etc. Further it is preferred to decrease the basic components in the carrier containing such inorganic component by calcination at high temperatures, washing with acid, washing with water, and the like means before use. Usually, the activity of the catalyst could decrease or the excellent effects of the heteropolyacid compound could be lost regardless of what the catalyst is supported on when the supported amount thereof is small because small supported amount leads to destruction of the structure of the heteropolyacid compound. Therefore, it is necessary to use the heteropolyacid in a larger supported amount or choose a carrier which will not destroy the structure of the heteropolyacid compound.

It is preferred to employ the catalyst in a reaction after pretreatment which is called as drying treatment including calcination and dehydration, activating treatment, etc., to form a catalyst preparation.

The hateropolyacid compound including that supported on a carrier usually contains moisture as water of crystallization, absorbed water, occluded water, etc., and high water content therefore, it is desirable to remove excess water from the heteropolyacid compound prior to using it as a catalyst.

Various drying methods can be used in order to remove excessive moisture in the heteropolyacid compound. Examples of such methods include a method for drying under reduced pressure and in the vicinity of room temperature for a long period of time, a method for drying in the air with heating at a temperature of, e.g., 100° C. or higher, a method for calcining in an atmosphere of a gas such as oxygen and nitrogen or under reduced pressure at a temperature, e.g., in the vicinity of 250° C., and a method for dehydrating by contacting a dessicant which will not deteriorate the catalytic activity. Any of these methods can be used.

Drying temperature various depending on the drying method within the range between room temperature and the temperature at which the structure of the heteropolyacid compound is destroyed, and usually 80° to 400° C., preferably 100° to 300° C.

The heteropolyacid compound which is used as a catalyst in the process of this invention regardless of whether or not subjected to the above-described drying treatment, can be activated by contacting it with an organic solvent or its vapor at room temperature or at elevated temperatures. Examples of the organic solvent include saturated hydrocarbons, aromatic hydrocarbons, alicyclic hydrocarbons and halogenated derivatives thereof.

Of these solvents, aromatic hydrocarbons are preferred. From the practical viewpoint it is particularly preferred to use the above-described aromatic hydrocarbons which are used as one of the starting materials.

The temperature for activation varies depending on the nature of organic solvents and the heteropolyacid compound, and usually it is in the range of 80° to 250° C., preferably 100° to 180° C.

If the activation temperature is too low the catalytic activity tends to be unsatisfactorily low or the induction period tends to become undesirably long. On the other hand, if the activation temperature is too high the catalyst to suffer various disadvantages such that considerable reduction of the catalyst takes place, the catalyst composition is decomposed, and the like. Therefore, the activation time is usually within 10 hours. Practically, it is preferably within 4 hours.

The catalyst used in the process of this invention can be used in the form of powder as it is or the powder can be shaped into granules, tips, balls, pellets, etc. In any case, it is preferred to adjust the particle size of the catalyst powder smaller than 60 mesh before shaping.

The amount of the catalyst to be used varies widely depending on the nature of starting materials, reaction temperature, pressure, etc. Usually, the amount of the catalyst component, i.e., the heteropolyacid compound, is 0.01% by weight or more preferably 0.2% by weight or more, based on the total weight of the reactants. If the amount of the catalyst component is below 0.2% by weight the reaction tends to proceed at a low rate and require a long period of time till completion and polymerization of alkenyl-aromatic hydrocarbon molecules increases relatively, and it is often the case that the yield of the objective compound, i.e., alkenyl aromatic hydrocarbon derivatives is undesirably low. Although no adverse effect against the reaction is observed when the amount of the catalyst is increased, it is preferred from economical viewpoint to use usually 10% by weight or less based on the total weight of the reactants.

In the present invention, the reaction between an aromatic hydrocarbon and an alkenyl-aromatic hydrocarbon is carried out by contacting and/or mixing the starting materials in the presence of the above described catalyst. It is preferred to maintain the concentration of the alkenyl-aromatic hydrocarbon in the reaction system at a level of 5% by weight or less. When the concentration is above 5% by weight, side reactions such as polymerization tend to increase considerably, resulting in decrease in the yield of the product. Therefore, it is usually preferable that the concentration of the alkenyl-aromatic hydrocarbon in the reaction system be adjusted to 3% by weight or less.

There is no limitation to the manner in which the reaction according to this invention is carried out and any of a batch method, a semi-batch method, and a flow or continuous method can be used. In the batch method, for example, an aromatic hydrocarbon and a solid catalyst which is activated by the above-described method (and optionally an inert solvent) are charged in a reactor and mixed with stirring, and then while maintaining the temperature at a reaction temperature and continuing stirring an alkenyl-aromatic hydrocarbon (starting material) and/or an inert solvent is added portionwise to the reaction mixture.

It is usually preferred that the amount of the alkenyl-aromatic hydrocarbon to be added be 20 to 55% by weight based on the total weight of all the substances to be added.

There is no limitation to the period of time of addition. However, it is advantageous to adjust it such that the concentration of the alkenyl-aromatic hydrocarbon is maintained at 3% by weight or less and it is possible to control the reaction temperature. Usually, the addition time is 10 minutes to 6 hours. It is also preferred to maintain the reaction temperature at predetermined level and continue stirring even after completion of addition of the alkenyl-aromatic hydrocarbon. Thus, the reaction time including a period of time required for addition and period of time for stirring after addition is usually about 15 minutes to about 8 hours.

In the process of this invention, the reaction temperature varies depending upon the nature of the catalyst and other conditions, but usually in the range of 20° to 230° C., and more preferably 100° to 155° C. The reaction at a temperature lower than 80° C. is sometimes disadvantageous since the reaction rate decreases. On the other hand, when the reaction proceeds at a temperature higher than 230° C., not only by-products in particular high boiling point products tend to be formed in increasing amounts but also serious deterioration of the catalyst tends to occur resulting in the loss of the activity in a short period of time.

There is no limitation to the reaction pressure, and usually the reaction is carried out at a self pressure of the reactor at a predetermined reaction temperature or at an atmospheric pressure.

The reaction can be carried out also in an atmosphere of an inert gas. In this case, it can proceed under pressure.

Any solvents can be used in the reaction as far as they are inert to the reactants and catalysts. Usually, saturated aliphatic hydrocarbons and saturated alicyclic hydrocarbons are used typical examples thereof include pentanes, hexanes, octanes, cyclohexane, methylcyclohexane, ethylcyclohexane, etc. Also, a portion of the aromatic hydrocarbon used as a starting material can be employed as a solvent similarly as in the case of inert solvents.

After completion of the reaction, the solid catalyst is removed from the reaction mixture by filtration and/or centrifugation, and the thus-treated reaction solution as it is or after washing with water optionally is followed by ordinary distillation preferably vacuum distillation to obtain a desired product, i.e., alkenyl-aromatic hydrocarbons or fractions containing them.

There is no limitation to the manner in which filtration is carried out. For example, a filtration method using a membrane filter or a ceramic filter, preferably that using a membrane filter or ceramic filter under reduced pressure or under pressure, can be used. It is preferred that filters have a pore diameter of 0.5 μm or less. By using such filtration method as above minute powder of the catalyst, if any, in the reaction mixture can be removed efficiently.

In the process of this invention, surprisingly, the filtrate is neutral (pH: about 7), and the concentration of heteropolyacid compound remaining in the filtrate can be decreased to a very low level, e.g., as low as several ppm or less.

Therefore, in the process of this invention, no neutralization treatment is needed and a step of washing with water may be eliminated. The solid catalyst recovered as by filtration can be reused repeatedly. The recovered catalyst can be reused as it is, or it can be regenerated by washing with the above-described inert solvent and then pretreating (drying and/or activating) prior to every reuse.

The alkenyl-aromatic hydrocarbon derivative according to the process of this invention corresponds to an adduct between an aromatic hydrocarbon and an alkenyl-aromatic hydrocarbon.

The product obtained according to the process of this invention usually include compounds represented by general formula (II)

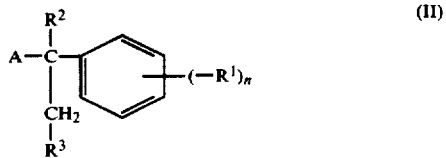

(II)

wherein $R^1$, $R^2$, $R^3$ and n have the same meanings as defined above, and A represents a non-condensed or condensed aromatic hydrocarbon radical.

This invention has the following benefits and advantages.

(1) According to this invention, the catalyst having a high catalytic activity and a high selectivity factor for a desired alkenyl-aromatic hydrocarbon derivative as compared with conventional catalysts is used in the production of alkenyl-aromatic hydrocarbon derivatives from an aromatic hydrocarbon and an alkenyl-aromatic hydrocarbon and as a result the process is extremely advantageous from economical viewpoint upon application on an industrial scale.

(2) The heteropolyacid compound used in this invention can be reused repeatedly for a desired reaction with less reduction in the catalytic activity. Therefore, this invention is very advantageous from the viewpoints of economy and ease of operation.

(3) Since this invention uses the heteropolyacid compound as a catalyst, separation of the catalyst from the reaction mixture can be carried out in a simple manner. This is, the separation can be attained substantially completely only by a simple, economical operation such as filtration. As a result, the catalyst used can be recovered simply and efficiently, thus enabling one to reuse the catalyst repeatedly and at the same time minimize the concentration of the catalyst in a filtrate to a level substantially negligible, resulting in that a step of removing the catalyst such as a step of washing with water can be eliminated. This invention provides a process for producing alkenyl-aromatic hydrocarbon derivatives which is very advantageous for using industrially on a large scale.

(4) Since the process of this invention uses the heteropolyacid compound as a catalyst, the reaction mixture after removal of the catalyst is neutral (ph: about 7) and therefore it is unnecessary to carry out neutralization treatment separately. This is one of the advantages when industrial application on a large scale is intended. Therefore, the process of this invention can eliminate steps of washing with water, alkali cleaning, disposing waste sulfuric acid and the like which are necessary in conventional processes using sulfuric acid or ion exchange resins, and thus procedures of this invention are simplified as compared with the conventional techniques. In addition, the process of this invention is economically advantageous in that the catalyst used has a long duration of life.

(5) Since the process of this invention uses the heteropolyacid compound as a catalyst, the catalyst can be activated by a very simple, practically advantageous pretreatment such as drying and/or treatment with starting material. This is also one of the advantages of this invention when it is used industrially on a large scale.

(6) In this invention, separation by filtration of the heteropolyacid compound from the reaction product can be facilitated considerably by allowing solid particles having a small particle size to coexist during the reaction. In this case, no substantial decrease in the catalytic activity and duration of life of the catalyst is observed.

(7) In the process of this invention, the heteropolyacid compound can be supported on a carrier. Doing so, the amount of the catalyst to be used can be minimized, and handling of the catalyst can be facilitated so that recovery of the catalyst from the reaction mixture can be carried out with ease.

Further, the catalyst used in the process of this invention is suited for flow process reaction, which is very advantageous from the viewpoints of economy and ease of operation in an industrial practice on a large scale.

As stated above, superiority of this invention in an industrial application over conventional processes is obvious to one skilled in the art.

This invention will be explained in greater detail with reference to Preparation Examples, Examples and Comparative Examples which are by way of example and by no means limit this invention.

PREPARATION EXAMPLE 1

Ten grams (10 g) of phosphotungstic acid ($H_3PW_{12}O_{40}\cdot nH_2O$) was allowed to stand in an atmosphere heated at 100° C. for 3 hours in order to dry it, and then was pulverized to prepare dry powder of the acid adjusted to grain size of #60 to #150 mesh.

PREPARATION EXAMPLE 2

Ten grams (10 g) of phosphotungstic acid was allowed to stand in a nitrogen gas atmosphere heated at 150° C. for 3 hours to calcine it, and then was pulverized to prepare dry powder of the acid adjusted to grain size of #60 to #150 mesh.

PREPARATION EXAMPLE 3

In a 200 ml glass reactor equipped with a stirrer and a reflux condenser were charged 100 g of Tetralin and 10 g of phosphotungstic acid. While stirring the contents of the reactor, the inner temperature was elevated to 150° C. and kept at that temperature for 3 hours. By this activation treatment the color of the catalyst turned into pink and thereafter into reddish brown.

PREPARATION EXAMPLE 4

Ten grams (10 g) of phosphotungstic acid and 1.41 g of cesium carbonate were dissolved separately each in 50 ml of water to obtain an aqueous solution of phosphotungstic acid (Solution A) and an aqueous solution of cesium carbonate (Solution B), respectively. While stirring Solution A, Solution B was added thereto portionwise. Thereafter, the mixture was evaporated to dryness at 90° C. and the resultant solid was pulverized and dried overnight at 150° C. to prepare cesium phosphotungstate acid salt having an atomic ratio of H:Cs:P:W:O = 1:5:2:24:80.

PREPARATION EXAMPLES 5-7

Procedures in Preparation Example 3 were repeated except that phosphotungstic acid was replaced by phosphomolybdic acid, silicotungstic acid, or silicomolybdic acid.

PREPARATION EXAMPLE 8

Procedures in Preparation Example 1 were repeated except that phosphotungstic acid was replaced by phosphomolybdic acid.

PREPARATION EXAMPLE 9

Ten grams (10 g) of silica gel (a product by Fuji Davison Co., Ltd., ID type, pulverized to grain size of #16 to #60 mesh) was heated at 150° C. in the air for 3 hours for drying. The thus-dried silica gel was immersed in an aqueous solution of 2 g of phosphotungstic acid in 50 ml of water and the resulting mixture was allowed to stand for 3 hours and evaporated to dryness at 80° C. Thereafter, the resulting solid was dried overnight at 130° C. to obtain a catalyst.

PREPARATION EXAMPLE 10

Procedures in Preparation Example 9 were repeated except that the silica gel was replaced by silica gel (a product by Fuji Davison Co., Ltd., MB3A, grain size of #30 to #200 mesh)to obtain a catalyst.

PREPARATION EXAMPLE 11

Ten grams (10 g) of alumina (a product by Daiya Cast Co., Ltd., DC-2282, grain size of #16 to #60 mesh) was heated in the air at 150° C. for 3 hours for drying. The thus-dried alumina was immersed in an aqueous solution of 2 g of phosphotungstic acid in 50 ml of water and allowed to stand for 3 hours. The solvent was evaporated to dryness at 90° C. and the resulting solid was dried overnight at 150° C. to obtain a catalyst.

PREPARATION EXAMPLE 12

Ten grams (10 g) of alumina (a product by Daiya Cast Co., Ltd., DC-2282, grain size of #16 to #60 mesh) was calcined in nitrogen gas at 450° C. for 3 hours. The thus-calcinated alumina was immersed in an aqueous solution of 2 g of phosphotungstic acid in 50 ml of water, and allowed to stand for 3 hours. The solvent was evaporated to dryness at 90° C. and the resulting solid was dried overnight at 150° C. to obtain a catalyst.

PREPARATION EXAMPLES 13 TO 16

Procedures in Preparation Example 9 were repeated except that the silica gel was replaced by alumina (a product by Daiya Cast Co., Ltd., DC-2282, grain size of #16 to #60 mesh, pulverized), activated carbon (a product by Mitsubishi Chemical Industries, Ltd., coal based granular DIAHOPE 006, grain size of #16 to #60 mesh), carbon black (a product by Mitsubishi Chemical Industries, Ltd., Carbon Black H), or titania (a product by Sakai Chemical Industry Co., Ltd., CS-700-24) to prepare catalyst preparations.

EXAMPLE 1

In a 200 ml glass reactor equipped with a stirrer, dropping funnel and a reflux condenser was charged 26.4 g of tetralin. While stirring the contents of the reactor, 1.1 g of the catalyst prepared according to Preparation Example 1 was added thereto, and the inner temperature was maintained at 150° C. Then, while stirring, a mixture of 10.4 g of styrene and 13.2 g of Tetralin was added dropwise at a rate of 0.23g/minute. After the stirring was continued for additional 30 minutes at 150° C., the stirring was stopped and the reaction mixture was filtered through a membrane filter having a thickness of 0.5 μm under reduced pressure to separate the catalyst from the reaction mixture. The reaction mixture was vacuum distilled in a still to obtain a product. On analysis, this product was identified as a mixture of 1-phenyl-1-(5, 6, 7, 8-tetrahydro-2-naphthyl) ethane represented by formula (III) and 1-phenyl-1-(5, 6, 7, 8-tetrahydro-1-naphtyl) ethane represented by formula (IV) in a molar ratio of 90:10. Purity was 95%.

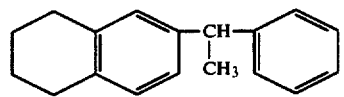 (III)

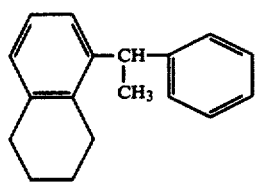 (IV)

The conversion of styrene and selectivity factor for products with respect to styrene are shown in Table 1 below. The products were colorless and odorless.

Analysis of the amount of residual catalyst in the filtrate reaction mixture indicated that only a small amount, i.e., 2 ppm of $H_3PW_{12}O_{40}$ was contained. The pH of the filtrate reaction mixture was 7.

EXAMPLES 2 TO 8 AND 10 TO 17

Procedures in Example 1 were repeated except that in place of the catalyst obtained in Preparation Examples 1, each of the catalysts prepared in Preparation Examples 2 to 8 and 10 to 16 was used in a prescribed amount shown in Table 1.

The results obtained are shown in Table 1.

EXAMPLE 9

Procedures in Example 1 were repeated except that 1.1 g of the catalyst obtained in Preparation Example 2 was used and the rate of addition of mixture of styrene and tetralin was changed to 1.0 g/minute. The catalyst separated and recovered was washed with 50 ml of hexane, and dried in the air at 100° C. for 30 minutes. The reaction was repeated using the catalyst thus recovered and dried. In this manner, the reaction was repeated 10 times in total with subsequent recovery and drying of the catalyst. The results obtained are shown in Table 2.

It is apparent from the results shown in Table 2 that the catalyst used in this invention exhibits substantially no decrease in the catalytic activity even after repetition of the reaction 10 times in view of the total amount of the catalyst lost during the experimentation (about 40% during 10 times of reactions). The pH of each reaction mixture was about 7.

EXAMPLES 18 TO 20

Procedures in Example 1 were repeated except that the catalyst obtained in Preparation Example 2 and the carriers obtained in Preparation Example 9, 13 and 14 were used in amounts of the catalyst and of solid having a small particle size shown in Table 1. The results obtained are shown in Table 1.

EXAMPLE 21

Procedures in Example 18 were repeated except that the catalyst recovered according to the procedures in Example 18 was used. The results are shown in Table 1.

While the invention has been described in detail and with reference to specific embodiments thereof, it will be apparent to one skilled in the art that various changes and modification can be made therein without departing from the spirt and scope thereof.

TABLE 1

| | Catalyst | | | Conversion of Styrene (%) | Selectivity (vs. styrene) (%) | pH of Filtrate | Remarks |
|---|---|---|---|---|---|---|---|
| | Heteropoly-acid (1) | Preparation Example | Amount (g) | | | | |
| Ex. 1 | $H_3PW_{12}O_{40}$ | 1 | 1.1 | 100 | 87 | Neutral (pH 7) | (2) |
| Ex. 2 | $H_3PW_{12}O_{40}$ | 2 | 1.1 | 100 | 88 | Neutral (pH 7) | |
| Ex. 3 | $H_3PW_{12}O_{40}$ | 3 | 1.1 | 100 | 89 | Neutral (pH 7) | |
| Ex. 4 | $H_{0.5}Cs_{2.5}PW_{12}O_{40}$ | 4 | 3.3 | 100 | 74 | Neutral (pH 7) | |
| Ex. 5 | $H_3PMo_{12}O_{40}$ | 5 | 0.70 | 100 | 69 | Neutral (pH 7) | |
| Ex. 6 | $H_4SiW_{12}O_{40}$ | 6 | 1.10 | 99 | 60 | Neutral (pH 7) | |
| Ex. 7 | $H_4SiMo_{12}O_{40}$ | 7 | 0.70 | 78 | 35 | Neutral (pH 7) | |
| Ex. 8 | $H_3PMo_{12}O_{40}$ | 8 | 0.70 | 72 | 24 | Neutral (pH 7) | |
| Ex. 9 | $H_3PW_{12}O_{40}$ | 2 | 1.1 | 100 (10 times) | 89–79 | Neutral (pH 7) | (3) |
| Ex. 10 | $H_3PW_{12}O_{40}$ (Carrier: $SiO_2$) | 9 | 1 | 100 | 85 | Neutral (pH 7) | (4) |
| Ex. 11 | $H_3PW_{12}O_{40}$ (Carrier: $SiO_2$) | 10 | 1 | 28 | 70 | Neutral (pH 7) | (4) |
| Ex. 12 | $H_3PW_{12}O_{40}$ (Carrier: $Al_2O_3$) | 11 | 3.5 | 100 | 84 | Neutral (pH 7) | (5) |
| Ex. 13 | $H_3PW_{12}O_{40}$ (Carrier: $Al_2O_3$) | 12 | 3.5 | 100 | 89 | Neutral (pH 7) | (5) |
| Ex. 14 | $H_3PW_{12}O_{40}$ (Carrier: $Al_2O_3$) | 13 | 2.5 | 100 | 54 | Neutral (pH 7) | (6) |
| Ex. 15 | $H_3PW_{12}O_{40}$ (Carrier: Activated Carbon) | 14 | 3.5 | 100 | 80 | Neutral (pH 7) | (7) |
| Ex. 16 | $H_3PW_{12}O_{40}$ (Carrier: Carbon Black) | 15 | 1 | 100 | 79 | Neutral (pH 7) | (4) |
| Ex. 17 | $H_3PW_{12}O_{40}$ (Carrier: $TiO_2$) | 16 | 3.5 | 100 | 68 | Neutral (pH 7) | (4) |
| Ex. 18 | $H_3PW_{12}O_{40}$ (Solid having a small particle size: $SiO_2$) | | Catalyst 0.5 g Solid 2 g | 100 | 78 | Neutral (pH 7) | |
| Ex. 19 | $H_3PW_{12}O_{40}$ (Solid having a small particle size: $Al_2O_3$) | | Catalyst 0.5 g Solid 2 g | 100 | 73 | Neutral (pH 7) | |
| Ex. 20 | $H_3PW_{12}O_{40}$ (Solid having a small particle size: Activated carbon) | | Catalyst 0.5 g Solid 2 g | 100 | 75 | Neutral (pH 7) | |
| Ex. 21 | Recovered catalyst of Example 18 (Solid having a small particle size: $SiO_2$) | | Catalyst 0.5 g Solid 2 g | 100 | 85 | Neutral (pH 7) | (8) |
| C. Ex. 1 | Ion exchange resin | | 6.6 | 100 (5 times) | 73–32 (5 times) | Acidic (pH 3–4) | (9) |
| C. Ex. 2 | Montmorillonite | | 6.6 | 97 | 26 | Neutral (pH about 7) | |
| C. Ex. 3 | La-substituted X type zeolite | | 6.6 | 95 | 38 | Neutral (pH about 7) | |
| C. Ex. 4 | Silica-Alumina | | 6.6 | 100 | 56 | Neutral (pH about 7) | |
| C. Ex. 5 | Silica-Alumina with | | 6.6 | 100 | 64 | Acidic | |

TABLE 1-continued

| | Catalyst | | | Conversion of Styrene (%) | Selectivity (vs. styrene) (%) | pH of Filtrate | Remarks |
|---|---|---|---|---|---|---|---|
| | Heteropoly-acid (1) | Preparation Example | Amount (g) | | | | |
| C. Ex. 6 | sulfuric acid impregnated Sulfuric acid | | 6.6 | 100 | 92 | (pH 1–2) Sulfuric acid contained | (10) |

(1) Indication of H₂O molecules was omitted for simplicity.
(2) Amount of H₃PW₁₂O₄₀ in the reaction mixture was 2 ppm.
(3) Repeated 10 times. Decrease in activity being low.
(4) 0.17 g of catalyst remaining.
(5) 0.58 g of catalyst remaining.
(6) 0.42 g of catalyst remaining.
(7) 0.58 g of catalyst remaining.
(8) Activity Increased.
(9) Reaction repeated 5 times. Activity deteriorated seriously.
(10) Long time needed to remove sulfuric acid.

TABLE 2

| | Number of Repetition of Reaction | | | | | | | | | |
|---|---|---|---|---|---|---|---|---|---|---|
| | 1 | 2 | 3 | 4 | 5 | 6 | 7 | 8 | 9 | 10 |
| Conversion of styrene | 100 | 100 | 100 | 100 | 100 | 100 | 100 | 100 | 100 | 100 |
| Selectivity (vs. Styrene) (%) | 89 | 86 | 87 | 83 | 84 | 86 | 83 | 80 | 79 | 81 |

EXAMPLE 22

Procedures in Example 2 were repeated except that instead of tetralin and styrene, 1-methylnaphthalene and p-methylstyrene were used as starting materials.

The product obtained was a mixture of a compound represented by formula (V) and a compound represented by formula (VI). The conversion (vs. p-methylstyrene) was 100% and the selectivity was 84%.

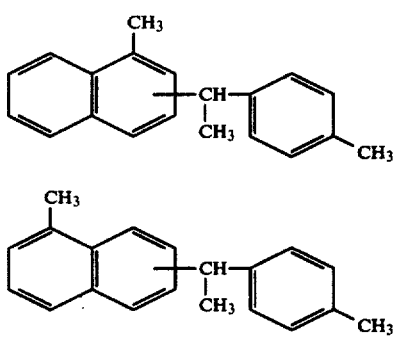

(V)

(VI)

EXAMPLE 23

Procedures in Example 2 were repeated except that in place of Tetralin, methyltetralin was used as a starting material.

The product obtained was a mixture of a compound represented by formula (VII) and a compound of formula (VIII). The conversion (vs. styrene) was 100% and the selectivity was 85%.

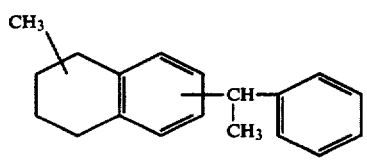

(VII)

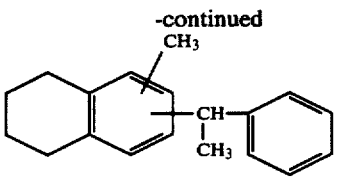

(VIII)

EXAMPLE 24

Procedures in Example 2 were repeated except that in place of Tetralin and styrene, naphthalene and α-methyl styrene were used as starting materials, and that α-methyl styrene was added with dilution.

The product obtained was a compound represented by formula (IX). The conversion (vs. α-methyl styrene) was 100% and selectivity was 52%.

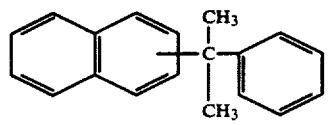

(IX)

EXAMPLE 25

Procedures in Example 2 were repeated except that in place of styrene, p-tert-butylstyrene was used as a starting material.

The product obtained was a product represented by formula (X). The conversion (vs, p-tert-butylstyrene) was 100% and the selectivity was 80%.

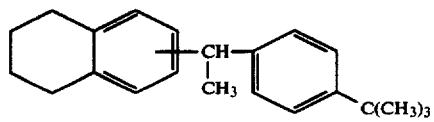

(X)

COMPARATIVE EXAMPLE 1

In a reactor were charged 48.7 g of Tetralin and 6.6 g of a cation exchange resin (Amberlist 15, a trade name for a product by Rhom & Haas Co.), and a mixture of 26 g of styrene and 17.3 g of tetralin was added thereto at a rate of 0.6 g/minute at a temperature of 102° C. The catalyst was recovered in the same manner as in Example 9. The reaction was repeated 4 times in total.

After completion of the 4th reaction, the catalyst recovered was regenerated with hydrochloric acid, brine, hydrochloric acid, and washing with water. Reaction was repeated using the thus-regenerated catalyst in the same manner as above. Thus, reaction was repeated 5 times in total with intervening recovery of or recovery and regeneration of the catalyst. The results obtained are shown in Table 1 and Table 3.

TABLE 3

|  | Number of Repetition of Reaction | | | | |
| --- | --- | --- | --- | --- | --- |
|  | 1 | 2 | 3 | 4 | 5 |
| Conversion of Styrene | 100 | 100 | 97 | 96 | 95 |
| Selectivity (vs. Styrene) | 73 | 62 | 37 | 37 | 32 |

From the results shown in Table 3 above, it can be seen that the catalytic activity was reduced to half the original after completion of the 3rd reaction. The pH of the reaction mixture was 3 to 4.

COMPARATIVE EXAMPLE 2

Procedures in comparative Example 1 were repeated except that the catalyst was replaced by montmorillonite catalyst obtained by treating commercially available one with sulfuric acid and pulverizing it into gramules. The results of the first reaction are shown in Table 1.

COMPARATIVE EXAMPLE 3

Procedures in Comparative Example 1 were repeated except that the catalyst was replaced by La-exchanged X type zeolite. The results of the first reaction are shown in Table 1.

COMPARATIVE EXAMPLE 4

Procedures in Comparative Example 1 were repeated except that the catalyst was replaced by a silica-alumina catalyst (NR 632 L, a trade name for a product by Nikki Chemical Co., Ltd.). The results of the first reaction are shown in Table 1.

COMPARATIVE EXAMPLE 5

Procedures in Comparative Example 1 were repeated except that the catalyst was replaced by one prepared according to Comparative Example 4 and subjected to sulfuric acid impregnation treatment by impregnating 100 ml of the catalyst in 200 ml of 50% sulfuric acid for one day one night, filtering the catalyst and then heating at 130° C. for 3 hours with stirring to carry out dehydration. The results of the first reaction are shown in Table 1.

COMPARATIVE EXAMPLE 6

Procedures in Example 1 were repeated except that the catalyst was replaced by 98% sulfuric acid and the reaction temperature was changed to 5° C.

After the stirring was stopped, it took 6 hours to separate substances derived by the action of sulfuric acid (e.g., sulfonated compound, etc.) as a sulfuric acid layer. It took 8 hours to separate water layer after the reaction solution was washed with an aqueous solution of alkali (10% sodium hydroxide). The conversion of styrene and the selectivity of product (vs. styrene) are shown in Table 1. Steps of neutralization and washing with water were necessary but the catalyst could not be used repeatedly. Further, it was necessary to dispose of waste sulfuric acid. Therefore, this process was found disadvantageous when applied to industrially on a large scale.

COMPARATIVE EXAMPLE 7

Procedures in Example 24 were repeated excepted that the catalyst was replaced by the catalyst prepared according to Comparative Example 5. The product obtained was a compound represented by formula (XI). The yield (vs. α-methyl styrene) was 41%.

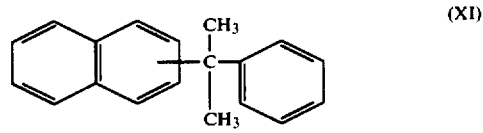

We claim:

1. A process for the preparation of an alkenyl-aromatic hydrocarbon derivative in an alkylation of an aromatic hydrocarbon by reacting an aromatic hydrocarbon with an alkenyl-aromatic hydrocarbon in the presence of a heteropolyacid and/or a salt thereof, which is characterized in that:

said heteropolyacid and/or salt thereof is subjected to an activation treatment by drying the heteropolyacid and/or the salt thereof under heating at a temperature of not lower than 100° C. or by immersing the heteropolyacid and/or the salt thereof in an aromatic hydrocarbon.

2. In the process according to claim 1, wherein said heteropolyacid is at least one member selected from the group consisting of phosphotungstic acid, silicotungstic acid, phosphomolybdic acid, and silicomolybdic acid.

3. In the process according to claim 2, wherein said heteropolyacid is used with a solid having a particle size smaller than 16 mesh.

4. In the process according to claim 3, wherein said solid is composed of at least one member selected from the group consisting of silica, alumina and activated carbon.

5. In the process according to claim 2, wherein said heteropolyacid is supported on a carrier.

6. In the process according to claim 5, wherein said carrier is at least one member selected from the group consisting of oxides of metals or semi-metals belonging to any one of Groups III, IV, V, VI, VII and VIII, complex oxides, activated carbon and carbon black.

7. In the process according to claim 5, wherein said carrier is at least one member selected from the group consisting of silica, alumina, titania, activated carbon and carbon black.

8. In the process according to claim 5, wherein said carrier has a pore diameter of 70 to 400 Å.

9. In the process according to claim 5, wherein said carrier has a pore diameter of 100 to 200 Å.

10. In the process according to claim 5, wherein said heteropolyacid is supported in an amount of 2% by weight or more based on the weight of.

11. In the process according to claim 1, wherein said heteropolyacid and/or salt is used in an amount of 0.01% by weight or more based on the total weight of all of the reactants.

12. In the process according to claim 1, wherein said reaction is carried out at temperature of 20° to 230° C.

13. In the process according to claim 1, wherein said heteropolyacid and/or salt is recovered after completion of said rection, and reused.

14. In the process according to claim 1, wherein said aromatic hydrocarbon is a non-condensed aromatic hydrocarbon containing one benzene ring or a condensed aromatic hydrocarbon containing one to three benzene rings, and alkenyl-aromatic hydrocarbon is represented by general formula (I).

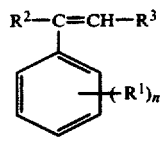

$$R^2-C=CH-R^3 \quad (I)$$

with $(R^1)_n$ on the benzene ring wherein $R^1$ represents a hydrogen atom or lower alkenyl group, $R^2$ and $R^3$, which may be the same or different, each represent a hydrogen atom, a methyl group or an ethyl group, and n is an integer of 1 or 2.

15. In the process according to claim 1, wherein said aromatic hydrocarbon is at least one member selected from the group consisting of tetralin, methyltetralin, naphthalene, and 1-methylnaphthalene, and said alkenyl-aromatic hydrocarbon is at least one member selected from the group consisting of styrene, p-methylstyrene, methylstyrene and p-tert-butylstyrene.

16. The process for the preparation of an alkenyl-aromatic hydrocarbon derivative in an alkylation of an aromatic hydrocarbon by reacting an aromatic hydrocarbon with an alkenyl-aromatic hydrocarbon in the presence of a heteropolyacid and/or a salt thereof, as claimed in claim 18, wherein:

said aromatic hydrocarbon is at least one element selected from the group consisting of tetralin, methyl tetralin, naphthalene and 1-methylnaphthalane; and said alkenyl-aromatic hydrocarbon is at least one element selected from the group consisting of styrene, p-methylstyrene, methylstyrene and p-t-butylstyrene, and at least one element selected from the group consisting of phosphotungstic acid, phosphomolybdic acid, silicatungstic acid, silicamolybdic acid, and/or salts thereof, which is produced by an activation treatment comprising drying the heteropolyacid and/or the salt thereof under heating at a temperature of not lower than 100° C. or immersing the heteropolyacid and/or the salt thereof in at least one aromatic hydrocarbon selected from the group consisting of tetralin, methyl tetralin, naphthalene and methylnaphthalane.

* * * * *

UNITED STATES PATENT AND TRADEMARK OFFICE
CERTIFICATE OF CORRECTION

PATENT NO. : 4,689,436

DATED : August 25, 1987

INVENTOR(S) : MINOKAMI ET AL

It is certified that error appears in the above-identified patent and that said Letters Patent is hereby corrected as shown below:

In the heading on the first page under "United States Patent [19]", "Minokani et al" should read---Minokami et al---.

Signed and Sealed this

Fifth Day of July, 1988

Attest:

DONALD J. QUIGG

*Attesting Officer*  *Commissioner of Patents and Trademarks*